United States Patent [19]

Williams

[11] 4,291,838

[45] Sep. 29, 1981

[54] NEBULIZER AND ASSOCIATED HEATER

[75] Inventor: Andrew S. Williams, Brea, Calif.

[73] Assignee: C. R. Bard, Inc., Murray Hill, N.J.

[21] Appl. No.: 107,062

[22] Filed: Dec. 26, 1979

[51] Int. Cl.³ .............................................. B05B 1/24
[52] U.S. Cl. .............................. 239/138; 128/203.27; 239/338
[58] Field of Search .................. 239/75, 136, 338, 370, 239/121, 137, 138, 139; 128/204.17, 203.27, 200.13, 200.18; 261/70, 119 R, 142, 130, DIG. 31–DIG. 33; 219/271–273, 275, 276, 311, 362

[56] References Cited

U.S. PATENT DOCUMENTS

| | | | |
|---|---|---|---|
| 3,652,015 | 3/1972 | Beall | 239/338 |
| 3,836,079 | 9/1974 | Hoston | 239/338 X |
| 3,859,398 | 1/1975 | Havstad | 219/275 X |
| 3,903,883 | 9/1975 | Pecina et al. | 128/203.27 |
| 3,915,386 | 10/1975 | Vora | 239/338 |
| 4,036,919 | 7/1977 | Komendowski et al. | 128/200.13 X |
| 4,051,205 | 9/1977 | Grant | 261/142 |
| 4,060,576 | 11/1977 | Grant | 261/142 X |
| 4,084,587 | 4/1978 | Lindsey | 128/200.18 |
| 4,101,611 | 7/1978 | Williams | 261/142 |

*Primary Examiner*—Robert B. Reeves
*Assistant Examiner*—Gene A. Church
*Attorney, Agent, or Firm*—Richard H. Zaitlen

[57] ABSTRACT

A nebulizer and heater system for delivering a heated aerosol spray to a patient. The nebulizer includes a nebulization chamber where an aerosol spray is formed and a subsequent heating chamber. Large liquid particles are collected in a well formed in the heating chamber. The heater is configured such that it can easily be joined to and removed from the nebulizer. The heater has a heating rod which extends into the well and heats the liquid collected therein. The heated liquid, in turn, heats the aerosol as it passes through the heating chamber.

13 Claims, 4 Drawing Figures

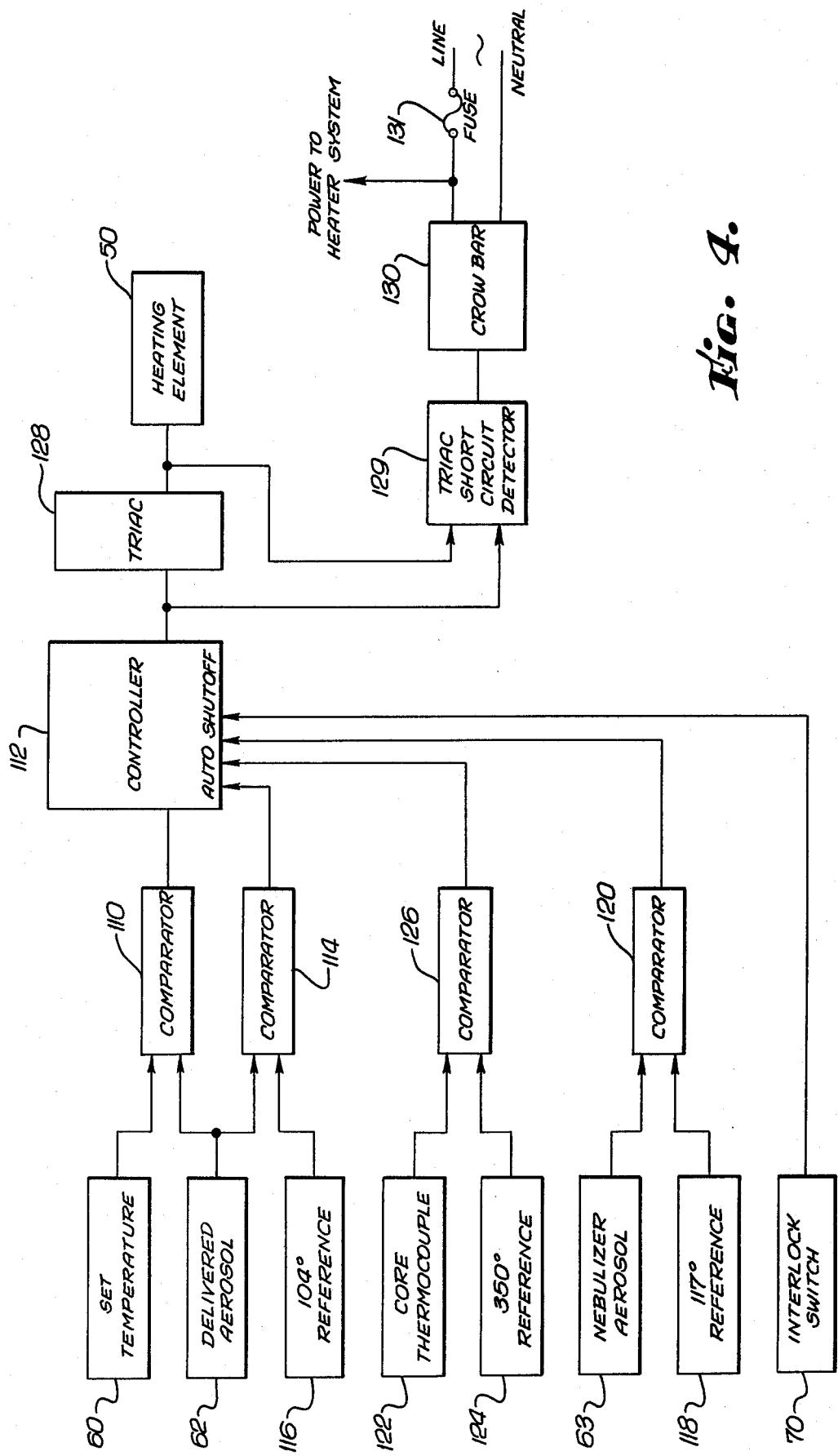

NEBULIZER AND ASSOCIATED HEATER

BACKGROUND OF THE INVENTION

1. Field of the Invention

This invention relates to a heating device in conjunction with an inhalation therapy device, and more particularly, to an electric heating device for heating an aerosol spray produced by a disposable nebulizer.

2. Prior Art

A number of respiratory ailments are treated by having the patient inhale an aerosol spray of finely divided particles of water or other liquid medicaments. Devices referred generally as nebulizer devices have evolved which are designed to produce such an aerosol spray. Nebulizers introduce a stream of pressurized gas, usually oxygen, into a chamber which entrains liquid particles so as to form the spray. Examples of these devices are shown in U.S. Pat. Nos. 3,652,015; 3,836,079; 3,915,386; and 4,036,919.

In order to prevent cross-contamination, it is generally preferred that a nebulizer be manufactured as a single use disposable device. In addition, the water supply which is used to form the aerosol is usually provided in a prefilled disposable bottle which is connected to the nebulizer. Since both the nebulizer and water supply bottle are disposable, their manufacturing cost must be kept low.

It has been determined that it is beneficial to the patient if the aerosol spray which is delivered is at or near body temperature. Since the water supply is generally at room temperature or below and some cooling occurs in the nebulization process, some type of external heating device is generally required. Most prior art heating devices are immersion type heaters which are placed directly in the water supply bottle and heat the entire water supply. As these heaters directly contact the water which will ultimately be delivered to the patient, the must be sterilized before each use. Systems which heat only a small portion of the water supply, just prior to nebulization, are shown in U.S. Pat. Nos. 3,903,833; 4,036,919; 3,864,544; 4,012,473; and 4,084,587. These devices, while providing improved performance over immersion type heaters, have certain drawbacks with respect to complexity or otherwise which has limited their acceptance.

It is a primary object of the present invention to provide a heater for use with a nebulizer which can be re-used, is easily attached and removed from the nebulizer and has no adverse effects upon the sterility of the nebulizer system.

Although all nebulizers appear to heat the water supply before the aerosol is formed, it is known to provide a means for heating liquid particles after they have been suspended in a gas, as is shown in U.S. Pat. Nos. 4,051,205 and 4,060,576. These patents are directed to humidifier systems which include a humidifier having a bottom humidification chamber containing a predetermined amount of liquid. The humidifier rests upon a "hot plate" type heater which heats the liquid in the humidification chamber, causing gas passing through the chamber to become humidified. The humidified gas is passed through a delivery hose which includes an integral heater. The use of a delivery hose with an integral heater presents sterilization and cost problems should re-use of the delivery hose be required. In addition, the hose is specifically designed to be used in conjunction with a humidified gas which has already been heated, as opposed to an unheated aerosol formed in a nebulizer. Furthermore, it is believed that the heating of the wet gas destroys aerosol mist particles and this would not be suitable for use with a nebulizer. It is a further object of the present invention to provide a nebulizer system in which all heating is accomplished within the nebulizer and which heats the aerosol spray formed in the nebulizer rather than the water supply which is used to create the aerosol.

SUMMARY OF THE INVENTION

The present invention provides a compact and efficient single stage heater which attaches to an associated nebulizer and heats the liquid to be delivered to a patient after it has been nebulized. The invention is specifically designed for use with a disposable nebulizer, an example of which is disclosed in copending application Ser. No. 060,393, filed July 25, 1979. This nebulizer is designed with an integral collection well in which larger droplets of liquid in the aerosol are collected. The collected liquid is referred to as the "rainout" from the aerosol. The nebulizer includes a nebulization chamber in which the aerosol is formed and a heating chamber downstream from the nebulization chamber. The collection well is formed as a part of the heating chamber.

Although the nebulizer of the present invention is preferably a disposable device, the heater is a relatively expensive item and is therefore designed for repeated use. In order to avoid the necessity of sterilizing the heater before each use, it is designed so that it does not come into direct contact with the aerosol. This is accomplished by providing an efficient heat transfer mechanism between the heater and the heating chamber of the nebulizer. The heater is comprised of a body which has an elongated heating element extending therefrom. The collection well of the nebulizer is fitted with a thin wall metal sleeve into which the heating element extends. The sleeve is isolated from the nebulizer housing by two silicon rubber gaskets which provide an effective water seal to prevent leakage of water from the collection well into the sleeve. In addition, the gaskets serve to insulate the nebulizer housing from excessive sleeve temperatures.

In operation, water precipitates out of the aerosol and collects in the collection well. The collected pool of water is heated by conduction from the heating element via the metal sleeve. The heated water in turn heats the aerosol stream passing over the well by addition of hot water vapor to the aerosol stream. The heated aerosol stream is then delivered to a patient.

The heater includes an integral solid state electronic controller to provide temperature control of the heating element. The controller utilizes a feedback system which controls the delivery of power to the heating element as a function of the temperature of the aerosol which is actually delivered to the patient rather than that which is present within the heating chamber. The controller also includes several safety features which remove power to the heating element in the event of the occurrence of a potentially dangerous situation. The first of these safety features includes an interlock switch located on the body of the heater which is closed only when the heater is properly attached to the nebulizer. The second safety feature removes power from the heating element when the temperature of the delivered aerosol exceeds a predetermined level, e.g., 104 degrees F. The third safety feature removes power from the heating element when the temperature of the aerosol within the heating chamber of the nebulizer exceeds a second predetermined temperature, e.g., 117 degrees F. This feature eliminates the possibility of delivering an overly hot mass of aerosol to a patient. In the absence of this feature, if gas flow through the nebulizer is cut off, the remaining gas and aerosol inside the nebulizer would be heated to a much greater degree than normal. When gas flow is restarted (e.g. after changing the water supply bottle), the hot aerosol would be immediately delivered to the patient. Typically, the delivered temperature may momentarily reach 125° F. The inclusion of the third feature prevents such temperatures from being reached. The final safety feature shuts off power to the heating element in the event that the temperature of the heating element itself rises above a predetermined temperature, e.g., 350° F. Such a rise in temperature might occur if the collection well runs dry.

Another safety feature of the present invention is an electronic circuit which detects a fault condition in the heater power control circuit. This circuit shuts off the heat completely by blowing a fuse in series with the heater power supply. Without this feature, the heater power control circuit would always supply full power to the heater power control circuit, thus rendering the temperature control system inoperative. The inclusion of this safety feature prevents excessive temperatures at the patient from being reached.

One advantage of the present invention is that only water precipitated from the aerosol, i.e., rainout, is heated. Thus, the temperature of the aerosol is not dependent upon the level of water in the supply bottle. In addition, since only a small amount of water is heated, response time of the heater to changes in temperature at the patient is short. Further, heating only the small volume of water in the collection well results in energy savings.

Another advantage of the present invention is that the heater can be joined to the nebulizer such that direct contact between the heater and the water is precluded. This mens that there is no need to sterilize the heater after each use. In addition, the lack of direct contact prevents corrosion of the heater. Finally, the heater is configured such that it can be easily attached to the nebulizer without complex mounting systems or the like.

The novel features which are believed to be characteristic of the invention, both as to its organization and method of operation, together with further objectives and advantages thereof, will be better understood from the following description considered in conjunction with the accompanying drawings in which a presently preferred embodiment is illustrated by way of example. It is to be expressly understood, however, that the drawings are for the purpose of illustration and description only and not intended as a definition of the limits of the invention.

BRIEF DESCRIPTION OF THE DRAWINGS

In the drawings, wherein like numbers refer to like parts:

FIG. 4 is a block diagram of the temperature controller and safety mechanisms of the present invention.

DETAILED DESCRIPTION OF THE INVENTION

Figure 1:
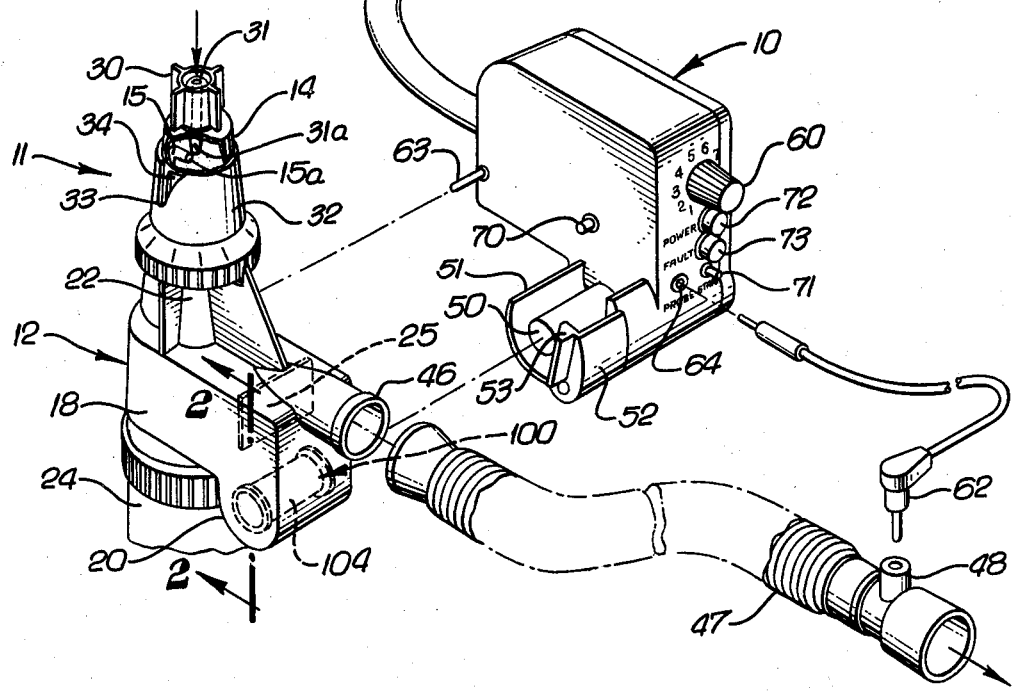
FIG. 1 is a partially exploded perspective view of the heater and a disposable nebulizer device for use therewith.
Figure 3:
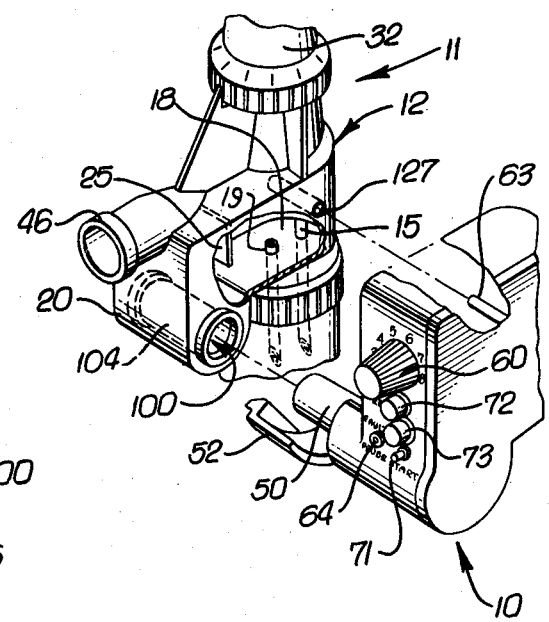
FIG. 3 is a second perspective view of the heater and nebulizer.

Referring to FIGS. 1 and 3, there is shown the electric heater 10 adapted to be joined to an associated nebulizer 11. The nebulizer 11 comprises a plastic body 12 which includes a tubular top section 14 defining a nebulization chamber, a generally rectangular bottom section 18 defining a heating chamber, and a tubular venturi section 22 formed therebetween. The nebulizer 11 is joined to a fluid supply bottle 24, only the top of which is shown in FIG. 1. The bottle 24 preferably contains a purified liquid, such as water, which may be medicated, and which is to be ultimately delivered to the patient in the form of an aerosol spray as hereinbelow described. In the nebulizer 11 shown in FIG. 1, the supply bottle 24 is attached to the bottom section 18 of the nebulizer 11 and water is initially delivered to the tubular top section 14 via a supply conduit 15 having a nozzle 15a at its end. A return connection from the bottom section 18 to the supply bottle 24 is provided by a drain tube 19 located at the bottom of the section 18.

Adjacent the top of the nebulizer 11 is a coupling 30 circumferentially disposed about a gas conduit 31. Coupling 30 is configured to be joined to a source of pressurized oxygen or air. Such couplings are well known in the art. Usually, 100% oxygen is utilized and is supplied at a pressure of up to 50 psi. The gas conduit 31 extends into the tubular top section 14 and has a nozzle 31a at its end which is perpendicular to and cooperates with the nozzle 15a to form a fine aerosol spray.

The tubular top section 14 of the nebulizer 11 defines a nebulization chamber in which the aerosol spray is produced. The aerosol spray is produced in a conventional manner and will not be described in detail. Basically, a stream of oxygen from the nozzle 31a is passed across the nozzle 15a. The passing of the oxygen by the nozzle 15a draws fluid from the supply bottle 24 up through the supply conduit 15 and through the nozzle shown in FIG. 1, a rotatable collar 32 having a pair of opposed openings 33 surrounds the top section 14. The top section 14 includes a pair of opposed openings 34. Rotation of the sleeve 32 brings the openings 33 into alignment with the openings 34. The passage of oxygen into the top section 14 causes outside air to be drawn through the openings 34 into the nebulization chamber. This reduces the oxygen content of the aerosol ultimately delivered to the patient. It should be understood that other nebulizer designs are within the scope of the present invention.

After the aerosol has been formed, it flows through the venturi section 22 and into the bottom section 18. The venturi 22 helps to increase the flow rate of ambient air into the device. On the bottom section 18, large particles are precipitated from the aerosol and collected in a collection well 20 which is integral with the bottom section 18. The precipitation is encouraged by a baffle plate 25 located within the bottom section 18. The precipitation of large particles is desirable as it is believed to be beneficial to deliver an aerosol spray of fine particles to the patient. After the aerosol passes through the bottom section 18, it is delivered to a patient via a outlet port 46 and a flexible conduit 47. Overflow from the collection well 20 will drain back into the supply bottle 24 via the drain tube 19.

Figure 2:
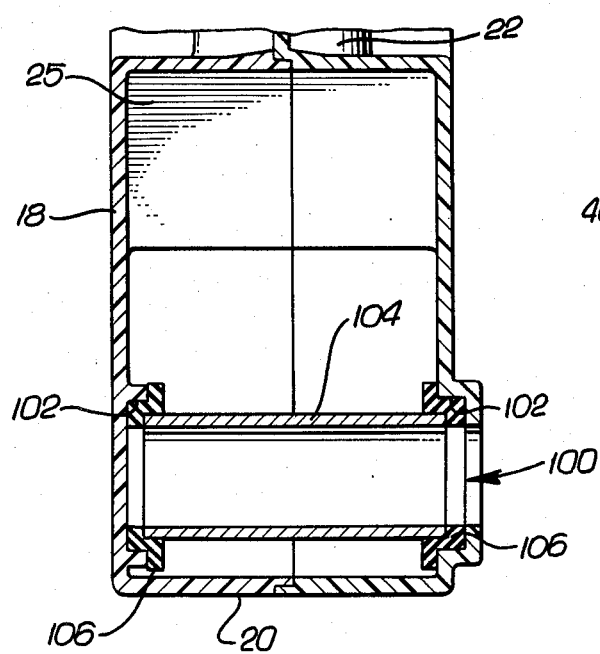
FIG. 2 is a cross-sectional view taken along lines 2—2 of FIG. 1, and showing the internal aspects of the electric heater sleeve of the present invention.

Referring now to both FIGS. 1 and 2, the collection well 20 has an opening 100 in one side wall. A tubular metal sleeve 104 extends into the opening 100 and across the collection well 20. A pair of water tight, heat resistant silicon rubber washers 106 are disposed about the ends of the sleeve 104 and are placed in an associated depression 102 formed on each of the side walls of the collection 20. Opening 100 and sleeve 104 enable the external heater 10 as described hereinbelow, to be readily joined to the nebulizer 11 such that the aerosol is heated as it passes through the bottom section 18 and over the collection well 20 prior to delivery to the patient.

The heater 10 includes a cylindrical resistance heating element 50 which is designed to be inserted within and contact the metal sleeve 104 of the nebulizer device 11. A plastic safety guard 51 is provided to prevent inadvertent touching of the heater element 50 either by a user or to a resting surface. The safety guard 51 fits the contour of the collection well and has a spring loaded latch 52 which when opened allows the heating element 50 to be slid into the sleeve 104 of the nebulizer 11. Once the heating element 50 is fully within the sleeve 104, the latch 52 may be returned to its closed position such that an integral ridge 53 overlaps the side of the collection well 20 opposite the heater 10.

Referring to FIGS. 1 and 3, the temperature of the heating element 50 is controlled by an electronic temperature control mechanism. Although a simple thermostat device could be used which regulates the temperatures of liquid in the collection well 20, it is preferred to employ a system which controls the temperature of the aerosol actually delivered to the patient. This is because the temperature of the aerosol mist which is delivered to the patient would be less than the temperature of the aerosol mist as it passes over the collection well 20. In order to regulate the temperature of the delivered aerosol, a thermistor probe 62 is positioned in an opening 48 near the end of the conduit 47. The thermistor probe is detachably connected to a socket 64 in the body of the heater 10. A control potentiometer 60 can be adjusted to a desired temperature.

In operation, a voltage proportional to the temperature of the delivered aerosol as determined by the thermistor probe 62 is compared to a voltage proportional to the temperature set on the control potentiometer 60 by means of a comparator 110. If the temperature of the delivered aerosol is lower than the set temperature, the comparator 110 will generate a signal to a integrated circuit zero voltage switching (ZVS) device controller 112 which controls a triac 128. The triace 128 in turn controls the amount of power supplied to the heating element 50. Various temperature controllers could be utilized in the present invention, and the controller 112 will not be described in detail herein. Power is supplied to the heating element 50 until the temperature of the delivered aerosol is equal to the set temperature. Typically, a regulation of plus or minus one degree C. or better is achieved.

The heater 10 includes several features designed for patient protection. If the aerosol temperature, as measured by thermistor probe 62, exceeds 104 degrees F., current to the heating element will be automatically removed. This is done by using a second comparator 114 to compare the voltage proportional to the temperature of the thermistor probe 62 with a reference voltage 116 representing the 104 degree limit. Similarly, a thermistor probe 63, located at the rear of the heater 10, is used in conjunction with a reference voltage 118 and a comparator 120 to prevent the aerosol temperature in the nebulizer 11 from rising above about 117 degrees F. The probe 63 engages with a small closed recess 127 located in the lower rear portion of the nebulizer body 12. The wall thickness of the recess 127 is thin enough for the probe 63 to detect the internal temperature of the nebulizer, yet strong enough to maintain the structural strength ad gas tightnes of the nebulizer body. If the flow of aerosol through the nebulizer 11 were temperarily halted for some reason and the heater 10 left on, the temperature within the bottom section 18 could rise drastically. This is because the temperature at the thermistor probe 62 would not be increasing when no aerosol is flowing past it. When the aerosol flow is recommenced, a blast of overly hot aerosol would be delivered to the patient, which could be extremely harmful. The use of the thermistor probe 63 prevents the temperature within the bottom section 18 from rising above a safe limit.

A third safety mechanism consists of a safety interlock switch 70 which is positioned on the heater 10 such that it is engaged by the body of the nebulizer 11 only when heater 10 is properly affixed to the nebulizer 11. The safety interlock switch 70 interrupts current to heating elememt 50 when the heater 10 is detached from the nebulizer 11.

A fourth safety mechanism causes power to the heating element 50 to be interrupted if the core of the heating element 50 rises above a predetermined value. Normally, the temperature of the element 50 would not rise above 212 degrees F., since it will be surrounded by water in the well 20. If the well 20 runs dry, however, the temperature of the heating element 50 will quickly rise. A core thermocouple 122 determines the temperature of the core of the heating element 50. A reference voltage 124 and comparator 126 are utilized to cause the controller 112 to remove power to the heating element in the event the core temperature rises above 350 degrees F.

Yet another safety mechanism causes interruption of power to both the heating element 50 and the control circuitry should the triac 128 become short circuited, which could cause the heating element 50 to be continuously powered. A short circuit detector 129 remains off while correct signals are seen at the input and output of the triac 128. If a short circuit condition should occur, the detector 129 delivers an enabling signal to a crowbar circuit 130. The crowbar 130 causes a momentary current flow though a power line fuse 131 which causes the fuse to oen, thus shutting down the entire system.

Thus, the heater 10 controls the temperature of the aerosol which is actually delivered to the patient rather than the aerosol which leaves the nebulizer 11. In addition, the heater 10 includes five safety shutoff mechanisms which remove power to the heating element 50. After removal of power, a reset switch 71 on the heater body must be activated to enable power to again be supplied to the heating element 50. In operation, heat from the heating element 50 is transmitted by conduction through the tubular sleeve 104, which in turn heats the pool of liquid in the collection well 20. As the aerosol mist generated by the nebulizer 11 passes over the heated liquid, it is heated by the addition of hot liquid vapor before flowing out through the tubular conduit 46 and then by way of the flexible conduit 47 to the patient. Power indicator light 72 shows when power is being supplied to the heating element 50, while fault indicator light 73 shows when a fault condition exists.

Because only liquid which is precipitated into collection well 20 is directly heated, the temperature of the aerosol is not dependent upon the level of water in the supply bottle 24. Further, only a small amount of liquid is present in the collection well 20, changes in temperature of the delivered aerosol can be quickly effected. Further, heating only the small volume of liquid in the collection well 20 results in energy savings.

The rubber gaskets 106 disposed about the ends of the sleeve 104 provide an effective water seal between the sleeve 104 and the plastic housing which forms the collection well 20, despite variations in temperature. The gaskets 106 also insulate the nebulizer housing from a rise in the temperature of the sleeve 104 in the event that the collection well 20 runs dry.

In summary, the present invention is directed to a nebulizer and detachable heater in which a heated aerosol spray is provided to a patient by heating the actual aerosol rather than the water supply. By heating the water after formation of the aerosol, a reduction in energy requirements and faster response to temperature changes are achieved. This is accomplished in the preferred embodiment by providing a collection well in the bottom section of the nebulizer in which a small amount of liquid is heated and heat then transferred from the heated liquid to the aerosol spray in the bottom section. The collection well includes a tubular metal sleeve into which an elongated heating element of the heater extends. Heat is transferred from the heating element to liquid in the collection well via the sleeve. Since the heating element never contacts the liquid in the collection well or the aerosol which is delivered to the patient, sterilization before re-use is not required.

A wide variety of materials, shapes and configurations for the heater and nebulizer can be used in this invention, and it should therefore be understood that changes can be made without departing from the true spirit or scope of the invention. For example, in the preferred embodiment, the body 12 of the nebulizer 11 is preferably made of a polycarbonate plastic material, but other materials are also within the scope of the present invention. The scope of this invention, therefore, is not to be limited to the specific embodiments discussed and illustrated herein.

I claim:

1. A nebulizer system for producing a heated aerosol spray for delivery to a patient comprising:
   an integral nebulizer having a nebulizer chamber, aerosol means for producing a liquid aerosol spray in the nebulizer chamber, means for supplying liquid to the aerosol means, a heating chamber located downstream of the nebulization chamber and in flow communication therewith, said heating chamber including an integral liquid collection well for collecting precepitation from the aerosol, a heat exchange sleeve extending into said collection well, the interior of the sleeve being isolated from the heating chamber, and an outlet port connected to the heating chamber for directing the aerosol out of the heating chamber; and
   a heater detachably connected to the nebulizer, said heating including a heating element extending into and contacting the sleeve for heating the aerosol as it passes through the heating chamber without direct contact between the heater and the aerosol, heating being transferred from the heating element to liquid in the collection well via the sleeve, said aerosol in turn being heated by said liquid.

2. The system of claim 1 wherein said sleeve is tubular and extends through said collection well and said heating element is cylindrical, said system further including a pair of insulating gaskets for connecting the ends of the sleeve to the collection well, said gaskets providing a watertight seal between the sleeve and the nebulizer and preventing transfer of heat from the sleeve to the nebulizer.

3. The system of claim 1 wherein said heater includes coupling means for releasably securing the heater to the nebulizer.

4. The system of claim 1 further including temperature regulating means for controlling the temperature of the heating element.

5. The system of claim 4 wherein the temperature regulating means includes remote measurement means for determining the temperature of the aerosol delivered to a patient, wherein the temperature of the heating element is regulated in response to said determined temperature.

6. The system of claim 5 wherein said temperature regulating means includes first overheating control means for interrupting power to the heating element if the temperature of aerosol delivered to the patient exceeds a predetermined value.

7. The system of claim 5 wherein the temperature regulating means includes second overheating control means for interrupting power to the heater element if the temperature of the heating element exceeds a predetermined value.

8. The system of claim 5 wherein the temperature regulating means includes a safety interlock, located on the heater, for interrupting power to the heating element whenever the heater is detached from the nebulizer.

9. The system of claim 5 wherein said temperature regulating means includes third overheating control means for interrupting power to the heating element if the temperature of said aerosol located in the heating chamber exceeds a predetermined value.

10. The system of claim 4 wherein said temperature regulating means includes a power control element for regulating the amount of power delivered to the heating element and fourth overheating control means for interrupting power to the heating element upon failure of the power control element.

11. A nebulizer system for producing a heated aerosol spray for delivery to a patient, comprising:
    a nebulizer having a nebulization chamber, means for producing a liquid aerosol spray, a heating chamber downstream of said nebulization chamber and in flow communication therewith, said heating chamber including an integral collection well for collecting precipitation from the aerosol, said collection well including a tubular sleeve extending therethrough, and an outlet port for directing the aerosol out of the heating chamber;
    a heater detachably connected to the nebulizer and including a heating element extending into the sleeve, said sleeve transferring heat from the heating element to the aerosol as it passes through the heating chamber;
    a delivery tube, connected to the outlet port, for delivering the heated aerosol from the nebulizer to a patient;

a temperature monitor located in the delivery tube for determining the temperature of aerosol; and control means connected to the temperature monitor for regulating the temperature of the heating element.

12. A method of producing a heated aerosol spray comprising the steps of:

providing a nebulizer having a heating chamber and a nebulization chamber, said heating chamber including a section configured to collect a pool of liquid;

providing a heater which is joined to said nebulizer and includes a heating element;

forming an aerosol spray in said nebulization chamber;

directing the aerosol spray into the heating chamber, where at least some of said aerosol precipitates and forms a pool of liquid in said heating chamber;

heating the pool of liquid with said heating element such that heat is transferred to the aerosol spray; and directing the heated aerosol out of the heating chamber.

13. A nebulizer system for producing a heated aerosol spray for delivery to a patient comprising:

an integral nebulizer having a nebulization chamber, aerosol means for producing a liquid aerosol spray in the nebulization chamber, means for supplying liquid to the aerosol means, a heating chamber located downstream of the nebulization chamber and in flow communication therewith, a heat exchange sleeve extending into the heating chamber, wherein the interior of the sleeve is isolated from the heating chamber, and an outlet port connected to the heating chamber for directing the aerosol out of the heating chamber;

a heater detachably connected to the nebulizer, said heater including a heating element extending into and contacting the sleeve for heating the aerosol as it passes through the heating chamber without direct contact between the heater and the aerosol; and coupling means for releasably securing the heater to the nebulizer, said coupling means including a safety guard covering the heating element and a latch attached to the safety guard and movable into engagement with the nebulizer to secure the heater to the nebulizer.

* * * * *